United States Patent [19]

Chmiel

[11] 4,008,710
[45] Feb. 22, 1977

[54] BLOOD PUMP

[76] Inventor: Horst Chmiel, No. 15, Brunnstrasse, 51 Aachen-Laurensberg, Germany

[22] Filed: Jan. 28, 1975

[21] Appl. No.: 545,000

[52] U.S. Cl. .................................... 128/1 D; 3/1.7
[51] Int. Cl.² .................................... A61M 1/03
[58] Field of Search .......... 128/1 D, 214 R, DIG. 3; 3/1.7

[56] References Cited
UNITED STATES PATENTS

| | | | |
|---|---|---|---|
| 3,327,322 | 6/1967 | Norton | 3/1.7 |
| 3,550,162 | 12/1970 | Huffman et al. | 128/1 D X |
| 3,668,708 | 6/1972 | Tindal | 3/1.7 |
| 3,723,754 | 3/1973 | Murayama et al. | 3/1 X |
| 3,726,762 | 4/1973 | Puharich | 3/1 X |
| 3,733,616 | 5/1973 | Willis | 3/1.7 |
| 3,766,567 | 10/1973 | Kahn et al. | 3/1.7 |

OTHER PUBLICATIONS

Arutsu et al., ASAIO, vol. XIV, pp. 323–327.
Robinson et al., ASAIO, vol. XIX, pp. 229–234.
Fourt et al., ASAIO, vol. XII, pp. 155–165.

Primary Examiner—Dalton L. Truluck
Attorney, Agent, or Firm—Neil F. Markva

[57] ABSTRACT

A blood pump comprises a rigid outer wall which defines a squeeze pump that is operated by a pumping medium. A valve mechanism is used for controlling the flow of blood through the pump. The squeeze pump includes a flexible pumping tube, an entry side and an exit side, entry side connection mechanism and an exit side connection mechanism. The entry side connection mechanism includes an atrium that is defined by the outer wall and includes a diaphragm forming an internal lining within the atrium. The lining diaphragm is separated from the rigid outer wall by the pumping medium used to operate the squeeze pump. The exit side connection mechanism includes a tube bend constituting a curvature of the aorta and has a diaphragm forming an internal lining within the tube bend. The internal lining of the tube bend is also separated from the rigid outer wall by the pumping medium. The cross-section of the atrium on the entry side is substantially circular and the flow of blood is directed tangentially into the atrium. Tube connections are provided to the atrium and the tube bend for directing pumping medium from these parts into an associated air sac alleviator. All parts of the pump which come into contact with the blood and are not covered by a lining are made of a material having a negative dipole moment.

9 Claims, 2 Drawing Figures

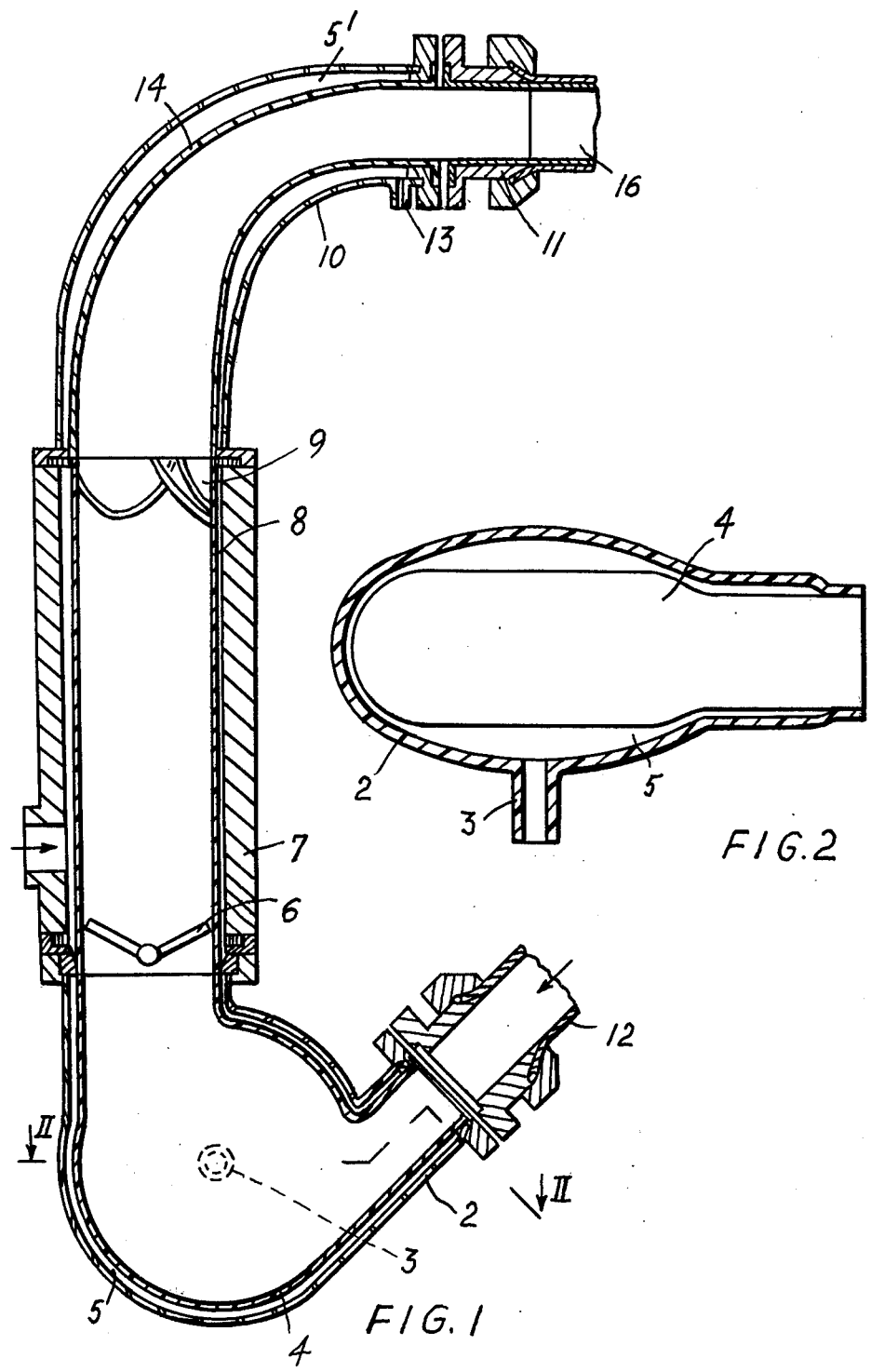

BLOOD PUMP

BACKGROUND OF THE INVENTION

The invention relates to a blood pump.

A blood pump which has been described in the patent literature comprises substantially a squeeze pump containing valves and operated by a pumping medium in the form of a pulsating fluid which separates a flexible pumping tube from a rigid outer wall, an atrium on the entry side and a tube bend on the exit side. The component parts of this pump which come into contact with blood are intended to be "compatible" with blood and it is proposed that they should consist of a specific material, namely "Dacron velour". However, this precaution is not yet sufficient since a negative surface charge of about 100 mV is also required. The prior proposal fails to provide for this need. At the Congress of the American Society for Artificial Internal Organs held in April 1973, Sawyer drew attention to this requirement. Another major objection to the above mentioned pump is the damage done to the blood by conditions of flow which are not physiological. The blood is highly stressed for shear and vacuum pressure in association with "stagnant pockets" destroy the red corpuscles (mechanical hemolysis). The proteins in the blood are denatured.

SUMMARY OF THE INVENTION

It is the object of the present invention to provide a blood pump which can remain in use for long periods, for instance for several days or even for several weeks. The need for such pumps in heart-lung machines and "artificial kidneys" is well known from the literature.

For achieving this object the present invention provides a blood pump which substantially comprises a rigid outer wall; squeeze pump having a flexible pumping tube and arranged to be operated by a pumping medium in the form of a pulsating fluid, said fluid separating the flexible pumping tube from the rigid outer wall; valves in the squeeze pump for controlling the flow of blood through said pump; an atrium on the entry side and a tube bend on the exit side of the squeeze pump, said tube bend constituting an "aortic arch"; a diaphragm forming an internal lining in the atrium excepting its entry connection, the atrium itself being substantially circular in plan and the blood entering the same tangentially; a further diaphragm which forms an internal lining in the tube bend, both lining diaphragms being separated from the rigid outer wall by a fluid of the same composition as the pumping medium and containing an anticoagulant to which the linings are permeable, and a pipe connection in the atrium as well as in the pipe bend each for an air sac alleviator, all parts of the blood pump which come into contact with blood, and which are not covered by a lining, being made of a material having a negative dipole moment.

A blood pump having a casing with a substantially circular portion which the blood enters in the tangential direction has already been disclosed. However, the circular part of the casing merely serves for maintaining the circular shape of the pumping tube in compliance with the shape of the cylindrical displacing piston in its direction of motion. This part of the casing therefore has nothing to do with the atrium of a blood pump according to the present invention. Moreover, the prior disclosure contains nothing suggesting that parts of the pump should be compatible with blood. This prior pump cannot therefore be compared with the pump of the present proposal.

According to yet another feature of the invention the diaphragm of the pump respectively the pumping tube has a wall which increases in thickness in pumping direction. This means that the tube will be compressed in the direction towards the tube bend, i.e., the aortic arch, to a decreasing extend so that the blood will be forced to flow in this direction.

The valves are preferably artificial heart valves available on the market and made of a material that also has a negative dipole moment. Such materials include for instance all those metals which in the electrochemical potential series have a high negative potential in relation to the hydrogen electrode, such as for instance titanium. Not only the heart valves, but preferably all the screw couplings are also made of this metal.

It is proposed to use heparin as the anticoagulant.

The permeability of the material of the diaphragm, i.e., of the pumping tube, to the anticoagulant, i.e., preferably heparin, causes a negative surface charge which would otherwise be absent to build up on those internal surfaces of the pump which come into contact with blood, excepting those parts, such as screw couplings and heart valves, which are made of titanium to provide the same effect.

However, the diaphragm is not only permeable to the anticoagulant, it is also highly flexible. Consequently it brings about a substantial improvement in the conditions of flow which would otherwise be non-physiological. For this reason the diaphragm on the entry side is spaced further away from the side walls than from the other walls of the surrounding atrium. This permits the sides of the diaphragm to yield to the pressure of the entering blood. The fluid thus displaced from the enveloping space enters an air sac alleviator from which it is returned when the pressure relaxes.

The entry opening, which is tangential to the atrium, in conjunction with the flexibility of the diaphragm and the circular shape in plan of the atrium result in the maintenance of a stationary vortex for as long as the entry valve is closed. The creation of an undesirable vacuum when the entry valve closes is thus avoided.

On the exit side, i.e., in what is known as the aortic arch, the expansion of the diaphragm towards the wall of the casing reduces the build-up of pressure peaks which would adversely affect the patient. This is assisted by the associated air sac alleviator which is designed to receive the fluid displaced from the jacketing space during expansion.

BRIEF DESCRIPTION OF THE DRAWING

Other objects of this invention will appear in the following description and appended claims, reference being made to the accompanying drawings forming a part of the specification wherein like reference characters designate corresponding parts in the several views.

FIG. 1 is a longitudinal sectional view through the center of the pump when placed on a flat surface such as a table, and FIG. 2 is a sectional view taken along line II — II of FIG. 1.

DESCRIPTION OF THE PREFERRED EMBODIMENT

A screw coupling 1 is made of titanium and connects a tube 12 for the supply of blood to an atrium or chamber within casing 2 which in the longitudinal sectional view has a cross-section that is a substantially circular shape. One of the end walls of the atrium 2 contains a central connection 3 for an auxiliary vessel in the form of an air sac alleviator. This may be of any desired conventional design and is not therefore illustrated. Its purpose will become apparent as the description proceeds.

The atrium 2 is lined with a highly flexible diaphragm 4 which is permeable to an anticoagulant, and which is separated from the rigid wall of the atrium 2 by a jacket 5 of liquid. This liquid contains the anticoagulant, which may be heparin, and which can diffuse through the diaphragm. A negative charge will therefore build up on the inside of the lining.

As will be understood from FIG. 2 the diaphragm 4 is spaced further away from the end walls of the casing 2 than from other casing parts. The parts of the diaphragm 4 facing the end walls can therefore elastically expand when subjected to internal pressure, in which case the volume of liquid displaced from the jacket 5 will be received into the above-mentioned auxiliary vessel via connection 3. In conjunction with a tangential entry of blood through a suitably arranged entry connection or coupling 1 a stationary vortex is maintained during the short periods an entry valve 6 closes. Undesirable vacuum pressures, "stagnant pockets" and so forth cannot therefore arise.

The atrium within casing 2 is adjoined by a pumping chamber 7. In conventional manner this contains a lining in the form of a flexible pumping tube 8 made of the same material as the diaphragm 4. The wall thickness of the pumping tube 8 increases in conveying direction, as is the usual practice. The pumping fluid also contains the anticoagulant, i.e. it is identical in quality with the liquid in the jacket 5 of the atrium casing 2. The presence of a negative surface charge is thus also ensured in this part of the pump.

The manner in which the pumping fluid is pulsed forms no part of the present invention and the pulsing means are not therefore shown.

Immediately after leaving the pumping tube 8 through an outlet valve 9, the blood enters an aortic arch defined by housing 10 where it returns through a flexible tube 16 attached to the arch by a second screw coupling 11, either directly into the patient's circulating system or into an associated apparatus such as an "artificial kidney" or an "oxygenator".

The aortic arch housing 10, like the atrium casing 2, is lined with a diaphragm 14 which is likewise spaced away from the wall. The diaphragm 14 can therefore yield should the internal pressure suddenly rise, displacing fuid contained in the jacket 5¹ into a second auxiliary vessel which, as in the case of the atrium, is attached to a pipe connection 13. The patient will not thus be exposed to undesirable pressure peaks.

A blood pump constructed as herein described avoids the shortcomings of conventional forms of construction, and it can operate for prolonged periods of time, for instance for several days and even for several weeks, without interruption. The cost of production of the two lining diaphragms including the pumping tube is so low that these elements can be regarded as being "disposables", in other words they need be used only once. No sterilization problems arise.

The invention may be embodied in other specific forms without departing from the spirit or essential characteristics thereof. The embodiment described and shown is therefore to be considered in all respects as illustrative and not restrictive.

What is claimed is:

1. A blood pump comprising:
   a. rigid outer wall means defining a squeeze pump being operated by a pumping medium and having a flexible pumping tube, an entry side and an exit side, entry side connection means and exit side connection means, and
   b. valve means for controlling the flow of blood through said pump,
   c. said entry side connection means including an atrium and a diaphragm means,
   d. said atrium being defined by said outer wall means and said diaphragm means forming an internal lining within the atrium,
   e. said lining diaphragm being separated from the rigid outer wall means by said pumping medium,
   f. said atrium is substantially circular in cross-section, and
   g. said entry side connection means includes means for directing the flow of blood tangentially into said atrium.

2. A blood pump as defined in claim 1 wherein the wall of the flexible tube of the pump increases in thickness in the pumping direction.

3. A blood pump as defined in claim 1 wherein the valve means comprise conventional artificial heart valves and are composed of a material that has a negative dipole moment.

4. A blood pump as defined in claim 1 wherein the pumping medium includes an anticoagulant to which the lining diaphragms are permeable, said anticoagulant being heparin.

5. A blood pump comprising:
   a. rigid outer wall means defining a squeeze pump being operated by a pumping medium and having a flexible pumping tube, an entry side and an exit side, entry side connection means and exit side connection means, and
   b. valve means for controlling the flow of blood through said pump,
   c. said entry side connection means including an atrium and a diaphragm means,
   d. said atrium being defined by said outer wall means and said diaphragm means forming an internal lining within the atrium.
   e. said lining diaphragm being separated from the rigid outer wall means by said pumping medium,
   f. said exit side connection means includes a tube bend constituting a curvature of the aorta and having a diaphragm forming an internal lining within the tube bend,
   g. said internal lining of the tube bend being separated from the rigid outer wall means by said pumping medium.

6. A blood pump as defined in claim 5 wherein said exit side connection means includes a tube connection for directing pumping medium from the tube bend into an associated air sac alleviator.

7. A blood pump comprising:
   a. rigid outer wall means defining a squeeze pump being operated by a pumping medium and having a flexible pumping tube, an entry side and an exit side, entry side connection means and exit side connection means, and
   b. valve means for controlling the flow of blood through said pump, c. said entry side connection means including an atrium and a diaphragm means,
d. said atrium being defined by said outer wall means and said diaphragm means forming an internal lining within the atrium,
e. said lining diaphragm being separated from the rigid outer wall means by said pumping medium,
f. said entry side connection means includes a first tube connection for directing pumping medium from the atrium into an associated air sac alleviator and
g. said exit side connection means includes a tube bend and a second tube connection for directing pumping medium from the tube bend into an associated air sac alleviator.

8. A blood pump comprising:
a. rigid outer wall means defining a squeeze pump being operated by a pumping medium and having a flexible pumping tube, an entry side and an exit side, entry side connection means and exit side connection means, and
b. valve means for controlling the flow of blood through said pump,
c. said entry side connection means including an atrium and a diaphragm means,
d. said atrium being defined by said outer wall means and said diaphragm means forming an internal lining within the atrium,
e. said lining diaphragm being separated from the rigid outer wall means by said pumping medium,
f. said atrium is substantially circular in cross-section,
g. said entry side connection means includes means for directing the flow of blood tangentially into said atrium,
h. said exit side connection means includes a tube bend constituting a curvature of the aorta and having a diaphragm forming an internal lining within the tube bend,
i. said internal lining of the tube bend being separated from the rigid outer wall means by said pumping medium,
j. said entry side connection means includes a first tube connection for directing pumping medium from the atrium into an associated air sac alleviator,
k. said exit side connection means includes a second tube connection for directing pumping medium from the tube bend into an associated air sac alleviator, and
l. all parts of said blood pump which come into contact with the blood being composed of a material having a negative dipole moment.

9. A blood pump as defined in claim 8 wherein said blood contacting parts are composed of titanium.

* * * * *